United States Patent [19]

van Zorge

[11] 4,297,359

[45] Oct. 27, 1981

[54] ANTI-ULCER COMPOSITIONS CONTAINING CERTAIN PYRIDYL OXIME ETHERS

[75] Inventor: Jacob A. van Zorge, Ameide, Netherlands

[73] Assignee: ACF Chemiefarma NV, Netherlands

[21] Appl. No.: 56,543

[22] Filed: Jul. 11, 1979

[30] Foreign Application Priority Data

Jul. 25, 1978 [GB] United Kingdom ............... 30951/78

[51] Int. Cl.³ .................. C07D 405/06; C07D 409/06; A61K 31/44
[52] U.S. Cl. .................... 424/263; 546/283; 546/284; 546/333
[58] Field of Search ................. 546/284, 283; 424/263

[56] References Cited

U.S. PATENT DOCUMENTS 3,205,234  9/1965  Schumann ........................... 546/338
3,290,320  12/1966  Villani ................................ 546/333

OTHER PUBLICATIONS

Rossi et al., Chem. Abstracts, vol. 61, No. 9, pp. 10545e–10546-d (1964).
The Merck Index, Eighth Edition, pp. 781–782, (1968).

*Primary Examiner*—Alan L. Rotman
*Attorney, Agent, or Firm*—Jacobs & Jacobs

[57] ABSTRACT

Pharmaceutical compositions having anti-ulcer activity, containing as an active ingredient a compound of the formula (I):

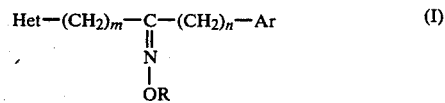

wherein Het is a pyridinyl group, Ar is a phenyl or a 5- or 6-membered monocyclic heteroaromatic group, and R is an alkyl, alkenyl, alkynyl, cyanoalkyl, carbamidoalkyl or aminoalkyl group, or an N-oxide thereof.

14 Claims, No Drawings

ANTI-ULCER COMPOSITIONS CONTAINING CERTAIN PYRIDYL OXIME ETHERS

This invention relates to pharmaceutical compositions having anti-gastric ulcer activity, to certain oxime ether derivatives for use in these compositions, and to methods for the preparation of these compounds.

In Farmaco. Ed. Sci. 19, 668–702 (1964), Chem. Abstr. 61, 10545e (1964), phenyl 2-pyridinyl ketone, O-dimethylaminoethyl oxime methiodide has been described, which compound showed acetylcholine antagonistic activity. The salts of the tertiary amine should possess papaverine-like activity in vitro.

In U.S. Pat. No. 3,205,234 a number of N-oxides of pyridinyl ketone O-hydrocarbon oximes have been mentioned, wherein the hydrocarbon group may be saturated or unsaturated acyclic aliphatic, cycloaliphatic, cycloaliphaticalkyl or araliphatic, containing up to twelve carbon atoms. The N-oxides are said to be active and useful as anti-inflammatory agents and drug-potentiators (e.g. potentiation of barbiturate-induced sleep in mammals), although this statement has not been supported by any pharmacological data.

According to this reference, these N-oxides are prepared by reacting a corresponding pyridinyl ketone O-hydrocarbon oxime with a peroxide. The starting oxime ethers are only described as intermediates. Thus, no pharmacological activity of these compounds has been mentioned.

In U.S. Pat. No. 3,290,320, which corresponds to British Pat. No. 1,070,964, phenyl 2-pyridinyl ketone, O-di(m)ethylaminoethyl/propyl oximes have been described, which compounds showed anti-androgenic activity.

In J. Pharm. Sci. 58, 138–141 (1969) phenyl 2-pyridinyl ketone, O-di(m)ethylaminoethyl oxime; 4-methoxyphenyl 2-thienyl ketone, O-dimethylaminoethyl oxime; and phenyl 2-picolinyl ketone, O-dimethylaminoethyl oxime have been described, which compounds showed anti-androgenic activity, but the effective dose was very close to the toxic dose.

It has now been found that certain oxime ethers derived from heterocyclic ketones possess anti-ulcer activity in the gastro-intestinal tract, e.g. by inhibition of gastric acid secretion and/or stimulation of mucus formation, and that pharmaceutical compositions containing them may be used in the treatment and/or prophylaxis of disorders of the gastro-intestinal tract.

The present invention provides a pharmaceutical composition having anti-ulcer activity, which composition comprises an anti-ulcer effective amount of a compound of the formula (I):

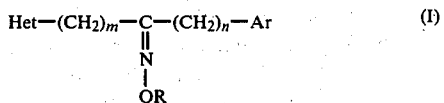

or an N-oxide thereof, or a pharmaceutically acceptable salt of said compound or said N-oxide, wherein
Het is a 2-, 3- or 4-pyridinyl group, or such group substituted by one or more halogen atoms or $C_{1-6}$ alkyl or $C_{1-6}$ alkoxy groups,
Ar is a phenyl or a 5- or 6-membered monocyclic heteroaromatic group, or such a group substituted by one or more halogen atoms or $C_{1-6}$ alkyl, $C_{1-6}$ alkoxy, trifluoromethyl or hydroxymethyl groups,
R is a $C_{1-3}$ alkyl, $C_{3-4}$ alkenyl, $C_{3-4}$ alkynyl, cyano $C_{1-3}$ alkyl, a carbamidoalkyl group with the formula $-(CH_2)_pC(O)NR^1R^2$, wherein p is 1 or 2, $R^1$ and $R^2$ are each hydrogen or $C_{1-3}$ alkyl, or $R^1$ and $R^2$ together with the nitrogen atom to which they are attached form a 5- or 6-membered heterocyclic ring in which another hetero atom may be present, or an aminoalkyl group with the formula $-(CH_2)_qNR^3R^4$, wherein q is 2 or 3, $R^3$ and $R^4$ are each hydrogen or $C_{1-3}$ alkyl, or $R^3$ and $R^4$ together with the nitrogen atom to which they are attached form a 5- or 6-membered heterocyclic ring in which another hetero atom may be present, and
m and n are each 0 or 1, with the proviso that m+n is not 2, in association with a pharmaceutically acceptable carrier or diluent.

Certain of the above compounds of formula (I) (and their N-oxides and addition salts) are believed to be novel and constitute a further aspect of the present invention. These compounds are those of formula (I) wherein Ar is a 5- or 6-membered monocyclic heteroaromatic group, or such a group substituted by one or more halogen atoms or $C_{1-6}$ alkyl, $C_{1-6}$ alkoxy, trifluoromethyl or hydroxymethyl groups. Suitable or preferred compounds of this group are hereinafter described in relation to the pharmaceutical compositions containing such compounds.

The compounds of formula (I) may be substituted or unsubstituted in Het, as described. However, it is believed that a preferred class of such compounds for their utility is that in which Het is unsubstituted.

Ar as a phenyl group is preferably unsubstituted phenyl.

Ar as a heteroaromatic group is preferably 2- or 3-thienyl, 2- or 3-furyl, 2- or 4-pyridinyl, of which 2-thienyl and 2-furyl are most preferred.

R is preferably R′ where R′ is methyl, ethyl, n-propyl, allyl, propargyl, cyanomethyl, dimethylaminoethyl or -propyl, of which $C_{1-3}$ alkyl, particularly methyl, and dimethylaminopropyl are most preferred.

Preferably, m and n are zero. If, however, n is one, the preferred of Ar is phenyl.

The pharmaceutically acceptable salts include the acid addition salt and quaternary addition salts. Among the therapeutically appropriate acids for the formation of additions salts are inorganic acids, such as hydrochloric acid, hydrobromic acid, sulphuric acid, nitric acid and phosphoric acid, and organic acids such as citric acid, acetic acid, oxalic acid, maleic acid, fumaric acid, lactic acid, succinic acid, tartaric acid and methanesulphonic acid, of which hydrochloric acid, sulphuric acid, maleic acid, fumaric acid and methanesulphonic acid are preferred.

It will be realized that each compound of formula (I) may exist in two different forms (E and Z-isomer). Both such forms are included within this invention. The compounds of the invention, as represented by formula (I), include free base and additions salt forms, separated isomeric forms and mixtures thereof.

Particularly preferred compounds within formula (I) in which Ar is phenyl include the 2-, 3- and 4-pyridinyl phenyl ketone, O-methyl, O-2-N,N-dimethylaminoethyl and O-3-N,N-dimethylaminopropyl oximes.

Particularly preferred compounds within formula (I) in which Ar is a heteroaromatic group include compounds of formula (I)′:

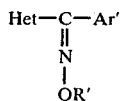   (I)' wherein Het is as previously defined, Ar' is 2-thienyl or 2-furyl and R' is methyl or dimethylaminopropyl.

Especially preferred compounds within the formula (I)' are: 2-pyridinyl 2-thienyl ketone, O-3-N,N-dimethylaminopropyl oxime, and 2-furyl 2-pyridinyl ketone, O-3-N,N-dimethylaminopropyl oxime.

The compounds (I) of the invention can be prepared according to methods which are known per se for the preparation of this type of compound or methods analogous thereto.

A suitable method for the preparation of a compound of formula (I) comprises the reaction of a compound of formula (II):

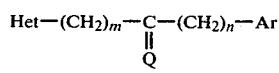   (II)

wherein Het, Ar, m and n are as defined in relation to formula (I) and C=Q is a carbonyl group or a protected carbonyl group, with a O-substituted hydroxylamine derivative of formula (III):

H$_2$N—OR   (III)

or a salt thereof, wherein R is as defined in relation to formula (I).

Suitable protected carbonyl groups are, for example, ketals and oximes. The preferred meaning of Q is oxygen. If Q is an alkylenedioxy group, it is preferably ethylenedioxy.

The reaction may be carried out under reaction conditions which are commonly used for this type of reaction. Preferably the reaction is carried out in a solvent, such as an alcohol, dioxane, dimethyl formamide, tetrahydrofuran or pyridine. Usually, the reaction temperature will be between room temperature and the boiling temperature of the reaction mixture.

The compound (III) is preferably added in the form of its acid salt, preferably its hydrochloride, to compound (II), which is preferably dissolved in pyridine.

A further suitable method for the preparation of a compound of formula (I) comprises the reaction of a compound of formula (IV):

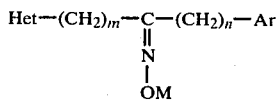   (IV)

wherein Het, Ar m and n are as defined in relation to formula (I) and M is a hydrogen or an alkali metal atom, with a compound of formula (V):

RY   (V)

wherein R is as defined in relation to formula (I) and Y is a suitable leaving group, such as a chloride, bromide, iodide or tosyloxy group.

The reaction may be carried out in a conventional solvent, such as methanol, ethanol, acetone, methyl ethyl ketone, dioxane, dimethylglycol ether or dimethyl formamide. If in formula (IV) M represents a hydrogen atom, it may be useful to add an acid binding agent to the reaction mixture. Suitable acid binding agents are, for example, alkali metal hydrides, hydroxides, carbonates and alkoxides, tertiary amines, pyridine and the like. The reaction conditions are as commonly used for this type of reaction. Usually, the reaction temperature will be between room temperature and the boiling temperature of the reaction mixture.

The conversion of the oxime compound (IV) into compound (I) is usually effected by alkylation with an alkyl, alkenyl, alkynyl, carbamidoalkyl, cyanoalkyl or (tert-amino)alkyl halide, such as the chloride, bromide or iodide, in the presence of, for instance, sodium hydride, an alkali metal hydroxide or alkoxide, preferably sodium methoxide, dissolved in a suitable solvent, preferably dimethyl formamide or methyl alcohol.

Generally, the preferred method of preparing any particular compound of formula (I) will depend to some extent on the compound itself.

It will be clear to those skilled in the art that, in a number of cases, certain reaction steps described may be carried out in a different sequence or simultaneously or without isolating intermediates, and these possibilities are all included in the invention. For example, the introduction of the group R in compound (I) according to the reaction of compound (II) with compound (III) may also be carried out by reacting compound (II) with a compound of formula (VI):

H$_2$N—OZ   (VI)

wherein Z is a group replaceable by or convertible into R, R being as hereinbefore defined. The compound of formula (VII) thus obtained:

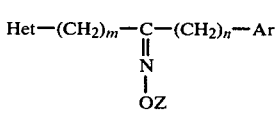   (VII)

wherein Het, Ar, Z, m and n are hereinbefore defined, can then be converted to the compound of formula (I).

The N-oxides of the compounds of formula (I) are preferably prepared by reacting a compound of formula (I) with a peroxide agent, for example, hydrogen peroxide, benzoyl peroxide, or a similar compound, of which hydrogen peroxide is preferred. The reaction is preferably carried out in an inert solvent, such as, for example, acetic acid, propionic acid, and the like, at temperature generally ranging between 50° C. and 90° C.

The N-oxides can also be prepared by reacting a compound of formula (II), wherein Het is the N-oxide of the previously defined hetero group (instead of the hetero group itself), with a hydroxylamine derivative of formula (III), in the manner hereinbefore described.

Pharmaceutically acceptable salts can be prepared from the compounds of the formula (I) in a conventional manner.

The intermediate compounds with formulae (II) and (IV) have been described in the literature or can be prepared by methods known per se.

Clearly the formulation of the pharmaceutical compositions of the invention will depend on the nature of the activity shown by the chosen compound of the formula (I), and on other factors such as a preference in a particular area of therapy for a particular mode of administration.

The compositions may be, for example, in the form of tablets, capsules, powders, granules, lozenges or liquid preparations, such as oral or sterile parenteral solutions or suspensions.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicles before use. Such liquid preparations may contain conventional additives such as suspending agents, emulsifying agents, non-aqueous vehicles (which may include edible oils) preservatives, and if desired conventional flavouring or colouring agents, and the like.

For parenteral administration, fluid unit dosage forms are prepared utilizing the compound of the formula (I) and a sterile vehicle. The compound, depending on the vehicle and concentration used, can be either suspended or dissolved in the vehicle. In preparing solutions, the compound can be dissolved for injection and filter sterilized before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions of this invention may be in the form of a microfine powder for insufflation.

As is common practice, the compositions will usually be accompanied by written or printed directions for use in the medical treatment concerned.

It will of course be realized that the precise dosage used in the treatment of any of the hereinbefore described disorders will depend on the actual compound of the formula (I) used and also on other factors such as the seriousness of the disorder being treated. Broadly, the dose may vary from about 100 mg up to about 25 g per day per patient.

The invention also provides a method of treatment and/or prophylaxis of gastric disorders in human beings which comprises the administration to the sufferer of an anti-ulcer effective amount of a compound of the formula (I), or an N-oxide thereof, or a pharmaceutically acceptable salt of said compound or said N-oxide.

Normally, the compounds of formula (I) will be administered as pharmaceutical compositions.

The "effective amount" will of course vary with factors such as the severity of the ulceration, the weight of the sufferer and the specific compound of the formula (I) used.

The following Examples illustrate the preparation of compounds of the formula (I) and their pharmacological properties.

EXAMPLE 1

Phenyl 4-pyridinyl ketone, O-methyl oxime

Phenyl 4-pyridinyl ketone (18.3 g) and O-methylhydroxylamine hydrochloride (12 g) dissolved in 200 ml of pyridine were refluxed for 8 hours. Pyridine was evaporated at reduced pressure and the residue was treated with chloroform and water. The chloroform layer was separated and dried over magnesium sulphate. Evaporation of the solvent afforded phenyl 4-pyridinyl ketone, O-methyl oxime as a 1:1 mixture of the E and Z-isomers (21.0 g), which was converted into the hydrochloride addition salts (m.p. 146°–149° C.).

If desired, the E and Z-isomers may be separated from the mixture by column chromatography (e.g. silica gel with cyclohexane-ethyl acetate 3:1 as the eluant). Identification of the isomers occurred by NMR.

In a similar manner the following compounds were prepared:

| | |
|---|---|
| phenyl 2-pyridinyl ketone, O-methyl oxime . HCl m.p. 149–152° C.(E-isomer) | (2) |
| phenyl 3-pyridinyl ketone, O-methyl oxime . HCl m.p. 97–99° C.(E-isomer) | (3) |
| phenyl 4-pyridinyl ketone, O-methyl oxime . HCl m.p. 188–190° C.(E-isomer) | (4) |
| 2-methylphenyl 2-pyridinyl ketone, O-methyl oxime, m.p. 97–99° C.(Z-isomer) | (5) |
| 4-methylphenyl 4-pyridinyl ketone, O-methyl oxime . HCl m.p. 155–170° C.(E:Z∼1:1) | (6) |
| 4-methoxyphenyl 4-pyridinyl ketone, O-methyl oxime . HCl m.p. 203–205° C.(dec.) (Z-isomer) | (7) |
| 4-fluorophenyl 4-pyridinyl ketone, O-methyl oxime . HCl m.p. 198–202° C.(Z-isomer) | (8) |
| 4-chlorophenyl 4-pyridinyl ketone, O-methyl oxime . HCl m.p. 195–200° C.(dec.) (Z-isomer) | (9) |
| 3,4-dichlorophenyl 4-pyridinyl ketone, O-methyl oxime . HCl m.p. 229–234° C.(dec.) | (10) |
| 2-pyridinyl 2-thienyl ketone, O-methyl oxime, oil (30% E, 70% Z-isomer) | (11) |
| 2-pyridinyl 3-thienyl ketone, O-methyl oxime, oil (40% E, 60% Z-isomer) | (12) |
| 3-pyridinyl 2-thienyl ketone, O-methyl oxime, oil (50% E, 50 & Z-isomer) | (13) |
| 4-pyridinyl 2-thienyl ketone, O-methyl oxime, m.p. 47–50° C.(25% E, 75% Z-isomer) | (14) |
| 2-furyl 2-pyridinyl ketone, O-methyl oxime, oil | (15) |
| phenyl 2-pyridinylmethyl ketone, O-methyl oxime . HCl m.p. 77–110° C. | (16) |
| di-2-pyridinyl ketone, O-methyl oxime, oil | (17) |
| 4-pyridinyl 4-trifluoromethylphenyl ketone, O-methyl oxime . HCl m.p. 183–185° C. | (18) |
| 4-hydroxymethylphenyl 4-pyridinyl ketone, O-methyl oxime, m.p. 97–100° C. | (19) |

EXAMPLE 2

Phenyl 4-pyridinyl ketone, O-cyanomethyl oxime

Phenyl 4-pyridinyl ketone oxime (5.4 g) was stirred in 50 ml of dimethyl formamide containing 1.5 g of a 50% dispersion of sodium hydride in oil, for 0.5 hours at room temperature. After the hydrogen evolution was completed, chloroacetonitrile (2.5 g) was added. The reaction mixture was stirred for 1 hour. The greater part of the dimethyl formamide was evaporated at reduced pressure, and then the residue was treated with ether and water. The ether layer was separated and dried over magnesium sulphate. The product was recrystallized from a mixture of ether and petroleum ether (40°–60° C.), yielding pure phenyl 4-pyridinyl ketone, O-cyanomethyl oxime (4.9 g, m.p. 101.5°–103° C.).

In a similar manner, the following compounds were prepared:

| | |
|---|---|
| phenyl 4-pyridinyl ketone, O-ethyl oxime . HCl m.p. 174.5–176° C. | (21) |
| phenyl 4-pyridinyl ketone, O-allyl oxime . HCl m.p. 164–165° C. | (22) |
| phenyl 4-pyridinyl ketone, O-propargyl oxime, m.p. 61–62° C. | (23) |
| phenyl 2-pyridinyl ketone, O-2-N,N-dimethylaminoethyl oxime . oxalate* m.p. 154–156° C. | (24) |
| phenyl 2-pyridinyl ketone, O-3-N,N-dimethylaminopropyl oxime . oxalate* m.p. 146–148° C. | (25) |
| phenyl 3-pyridinyl ketone, O-2-N,N-dimethylaminoethyl oxime, oil, b.p. 143°C./0.01 mm | (26) |
| phenyl 3-pyridinyl ketone, O-3-N,N-dimethylaminopropyl oxime, oil, b.p. 147° C./0.01 mm | (27) |
| phenyl 4-pyridinyl ketone, O-2-N,N-dimethylaminoethyl oxime . 2 HCl m.p. 191–193° C.(dec.) | (28) |
| phenyl 4-pyridinyl ketone, O-3-N,N-dimethylaminopropyl oxime . 2 HCl m.p. 197–200° C. | (29) |
| 2-pyridinyl 2-thienyl ketone, O-3-N,N-dimethylaminopropyl oxime, oil | (30) |
| 2-furyl 2-pyridinyl ketone, O-3-N,N-dimethylaminopropyl oxime, oil | (31) |

*The preparation of compounds (24) and (25) has been described in U.S. Pat. No. 3,290,320. However, no melting points were mentioned in said patent.

EXAMPLE 3

Phenyl 4-pyridinyl ketone, O-methyl oxime, N-oxide (Z-isomer)

A mixture of 9.1 g of phenyl 4-pyridinyl ketone, O-methyl oxime, 40 ml of glacial acetic acid and 15 ml of 30% hydrogen peroxide in water was heated overnight on a water bath at a temperature of 70° C. The reaction mixture was concentrated at reduced pressure, treated with chloroform and a saturated aqueous solution of sodium bicarbonate. The chloroform layer was separated and dried over magnesium sulphate. Evaporation of the solvent and successive crystallization from a mixture of ether and petroleum ether (40°–60° C.) afforded the title compound (6.2 g, m.p. 98°–99° C.).

Pharmacological Data

1. Effects on Gastric Secretion in the Pyloric Ligated Rat

The method as described by Shay et al. (Gastroenterol. 26, 906 (1945)) was used. After overnight starvation the pylorus of a rat was ligated under halothane aenesthesia and the compound under test or vehicle only administered intraduodenally and the rats allowed to recover. They were sacrificed three hours later and the gastric juice removed. After measurement of the volume of secretion, its hydrogen ion concentration, [$H^+$], was determined by titration with 0.5 n NaOH to pH 7. Groups of 4–6 animals were used for each treatment and the inhibitory effect of the compound was ascertained by comparison of the mean values obtained with those from a simultaneously set up control group of animals which received vehicle only. Students 't' test was applied for significance between groups. The mean values for % inhibition obtained for a number of experiments are shown in the following Table 1, the dosage being 100 mg/kg i.d.

2. Anti-ulcer activity

This was assessed by the inhibition of indomethacin induced gastric damage in the rat according to the method of Elegbe (Israeli J. Med. Sci. 10, 1451 (1974)).

Rats were starved overnight, given indomethacin subcutaneously (15 mg/kg) and sacrificed 5 hours later. Stomachs were inflated with 0.9% saline, cut along the greater curvature, pinned out and scored for gastric damage by the following system:

Score 1–3 according to the degree of erythema and slight haemorrhage.

Score 4–6 according to the degree of mucosal erosion.

Score 7–9 according to the depth of gastric damage. Groups of 7 rats were used for each treatment level of the compound under test and a similar group receiving vehicle only was set up on each occasion of testing. Compound or vehicle was administered orally 30 minutes prior to, and at 2 hours after dosing with indomethacin. Mean values per treatment were obtained using the above scoring system and the Mann Witney test applied for significance between such values. The mean inhibition of gastric damage from a number of experiments is shown in the following Table 2; the dosage being 100 mg/kg orally.

| | Table 1 % Inhibition | | Table 2 |
|---|---|---|---|
| Compound No. | Volume | [$H^+$] | % Inhibition |
| 1 | 82 | 41 | 86* |
| 2 | 76 | 33 | 79* |
| 3 | 87 | 50 | 82* |
| 4 | 82 | 50 | 77 |
| 6 | 81 | 89 | 80 |
| 7 | | | 88 |
| 8 | 76 | 11 | 100 |
| 9 | | | 80 |
| 10 | | 49 | |
| 11 | 84 | 36 | 78 |
| 12 | 78 | 20 | 100 |
| 14 | | | 77 |
| 16 | 46 | 25 | 72 |
| 17 | 83 | 14 | 76 |
| 18 | 59 | | |
| 19 | 66 | 35 | 71 |
| 20 | | | 96 |
| 21 | 77 | 24 | 100* |
| 22 | 76 | | 79 |
| 23 | 81 | | |
| 24 | 81 | 36 | 100 |
| 25 | 91 | 65 | 77 |
| 26 | 84 | | |
| 27 | 85 | | |
| 28 | 83 | 92 | 92 |
| 29 | 72 | 45 | 65 |
| 30 | 78 | 64 | 77 |
| 31 | 70 | 30 | 92 |
| 32 | 84 | 32 | 64 |

*50 mg/kg

What I claim is:

1. A compound selected from the group consisting of (a) a pyridine compound of the formula:

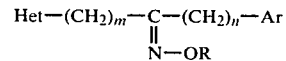

wherein
Het is pyridin-2-yl, pyridin-3-yl, or pyridin-4-yl, unsubstituted or substituted with halo, alkyl of 1 to 6 carbon atoms or alkoxy of 1 to 6 carbon atoms;
Ar is thien-2-yl, thien-3-yl, fur-2-yl or fur-3-yl unsubstituted or substituted with halo, alkyl of 1 to 6 carbon atoms, alkoxy of 1 to 6 carbon atoms, trifluoromethyl or hydroxymethyl;

R is alkyl of 1 to 3 carbon atoms, alkenyl of 3 or 4 carbon atoms, alkynyl of 3 or 4 carbon atoms, or

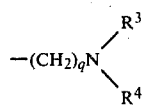

wherein q has a value of 2 or 3 and each of $R^3$ and $R^4$ independently of the other is hydrogen or alkyl of 1 to 3 carbon atoms; and each of m and n is 0 or 1, the sum of m and n being less than 2;

(b) the N-oxides thereof and (c) the pharmaceutically acceptable acid addition and quaternary addition salts of said pyridine compounds or said N-oxides thereof.

2. A compound according to claim 1 wherein R is methyl, 2-dimethylaminoethyl or 3-dimethylaminopropyl.

3. A compound according to claim 1 wherein Het is pyridin-2-yl.

4. A compound according to claim 1 wherein Ar is thien-2-yl.

5. A compound according to claim 1 wherein Ar is fur-2-yl.

6. The compound according to claim 1 which is pyridin-2-yl thien-2-yl ketone O-methyloxime.

7. The compound according to claim 1 which is pyridin-2-yl thien-3-yl ketone O-methyloxime.

8. The compound according to claim 1 which is pyridin-3-yl thien-2-yl ketone O-methyloxime.

9. The compound according to claim 1 which is pyridin-4-yl thien-2-yl ketone O-methyloxime.

10. The compound according to claim 1 which is pyridin-2-yl thien-2-yl ketone O-dimethylaminopropyloxime.

11. The compound according to claim 1 which is pyridin-2-yl fur-2-yl ketone O-methyloxime.

12. The compound according to claim 1 which is pyridin-2-yl fur-2-yl ketone O-3-dimethylaminopropyloxime.

13. A pharmaceutical composition for the treatment of gastric ulcers which comprises an effective amount of a compound according to claim 1 in combination with a pharmaceutical carrier.

14. The method of treating gastric ulcers in humans which comprises administering thereto an effective amount of a compound according to claim 1.

* * * * *